United States Patent [19]
Sgourakes et al.

[11] Patent Number: 5,146,793
[45] Date of Patent: Sep. 15, 1992

[54] FLUID SEAL

[75] Inventors: George E. Sgourakes, Millis; Stanislaw Koziol, Wrentham, both of Mass.

[73] Assignee: Millipore Corporation, Bedford, Mass.

[21] Appl. No.: 418,103

[22] Filed: Oct. 6, 1989

[51] Int. Cl.$^5$ ................................ B01L 3/02
[52] U.S. Cl. ................ 73/864.21; 277/138; 277/139; 277/216; 277/217
[58] Field of Search .......... 73/864.81–864.87, 73/864.21; 277/31, 45, 46, 84, 138–140, 149, 196, 216, 217, 223, DIG. 8

[56] References Cited

U.S. PATENT DOCUMENTS

| | | | |
|---|---|---|---|
| 2,211,899 | 8/1940 | Kriegbaum | 277/223 |
| 3,061,320 | 10/1962 | Haensch | 277/84 |
| 4,094,196 | 6/1978 | Friswell | 73/864.21 |
| 4,526,387 | 7/1985 | Flower | 277/198 |
| 4,739,997 | 4/1988 | Smetana | 277/216 |

Primary Examiner—Robert Raevis
Attorney, Agent, or Firm—Andrew T. Karnakis; Paul J. Cook

[57] ABSTRACT

A sealing means is provided that may be used, among other things, for sample injection apparatus used in liquid chromatography. The seal includes a jacket having a central bore through which a hypodermic needle containing a sample is inserted. The jacket includes a U-shaped cross section having an inner axial surface and an outer axial surface. Metal cylindrical bands which function as springs are positioned tightly against the inner and outer axial surfaces respectively. Each band has a slot extending through its thickness and along its entire axial length.

2 Claims, 3 Drawing Sheets

FLUID SEAL

BACKGROUND OF THE INVENTION

This invention relates to a seal construction and, more particularly, to a liquid chromatographic apparatus utilizing the seal construction.

In various analytical procedures, including liquid chromatography, a large number of liquid samples are Processed sequentially in the same apparatus. In these processes, a conduit such as a hypodermic needle is immersed sequentially in a series of different samples which are interspersed with a cleansing solvent so that there is no cross sample contamination within the apparatus due to a portion of a sample processed in an earlier step being admixed with a subsequently processed sample.

As disclosed in U.S. Pat. Nos. 3,916,692; 4,094,195 and U.S. Pat. No. 4,094,196 sample injection means for liquid chromatographic apparatus are utilized which include a reciprocating sampling conduit in the form of a hypodermic needle. The needle is adapted to enter a series of sample containers sequentially so that the samples can be delivered to a downstream liquid chromatographic apparatus with a solvent under pressure. The flow of solvent is controlled so that it carries the sample to the liquid chromatographic apparatus and so that it cleans the liquid pathway so that subsequentially processed samples are not contaminated. In these chromatographic processes, liquids are processed at pressures up to 6,000 psig and even higher. Accordingly, when processing a sample, its flow must be confined, as much as possible, to the hypodermic needle carrying the sample and to the pathways leading to the downstream chromatographic apparatus. Accordingly, it is essential that suitable sealing means be included in the sample handling apparatus.

These seals are positioned concentric to the bore of the injection apparatus through which the sample passes by means of an hypodermic needle. The seals also are positioned above and below a hole in the needle which is the point of injection of the sample from the hypodermic needle into the high pressure solvent stream. By operating in this manner, the injected sample is contained by the seals thereby eliminating contamination of subsequently processed samples.

It has been proposed to utilize seals positioned concentric within the bore which seals comprise a jacket having a U-shaped cross section into which is positioned an energizing means such as a spiral wound spring, a U-shaped metal wedge or an O-ring made from an elastomeric material. These energizers tend to spread the walls of the U-shaped cross section so that the jacket walls bear upon the inner surface of the bore and on the outer surface of the hypodermic needle passing through the bore thereby to effect the seal. The spiral wound and U-shaped energizers are undesirable since they provide low values of a non-uniform pressure along the axial length and circumference of the jacket within which they fit so that there are areas of low pressure along the axial lenght of the jacket which may cause leakage. The O-ring energizers are undesirable since they are formed of elastomeric materials which are prone to lose sealing pressure as a result of creep with time or cyclical exposure to temperature.

Accordingly, it would be desirable to provide a sealing means capable of withstanding all the pressures encountered during liquid chromatographic processes and which provide uniform pressure along the axial length and circumference of the seal through which a hypodermic needle carrying a sample passes.

SUMMARY OF THE INVENTION

The present invention provides a fluid seal Particularly useful in liquid chromatography apparatus which seals against leakage of a sample injected into a high pressure liquid stream. The fluid seal comprises a jacket having a central bore and a wall having a U-shaped cross section coaxial with the bore. Two cylindrical bands are positioned within the U-shaped cross section to fit tightly about the axial walls of the U-shaped cross section. Each cylindrical band includes a slot which extends through its thickness and along its entire axial length so that the cylinderal bands are capable of expanding or contracting. A liquid sample is injected from an outlet within a hypodermic needle which extends through the bores of the seals. The seals are positioned both above and below the point of injection from the hypodermic needle into a high pressure liquid stream which flows radially relative to the hypodermic needle. These seals fit within a bore through which the needle extends and one cylindrical band causes one wall of the U-shaped cross section of the jacket to fit tightly against the inner surface of the larger bore and the second cylindrical band causes a second wall of the U-shaped cross section to fit tightly about the hypodermic needle which extends through the bore of the jacket. The seals of this invention provide excellent sealing capability and maintain this sealing capability with extended use of presently available liquid chromatography injection apparatus.

DESCRIPTION OF SPECIFIC EMBODIMENTS

Figure 1:
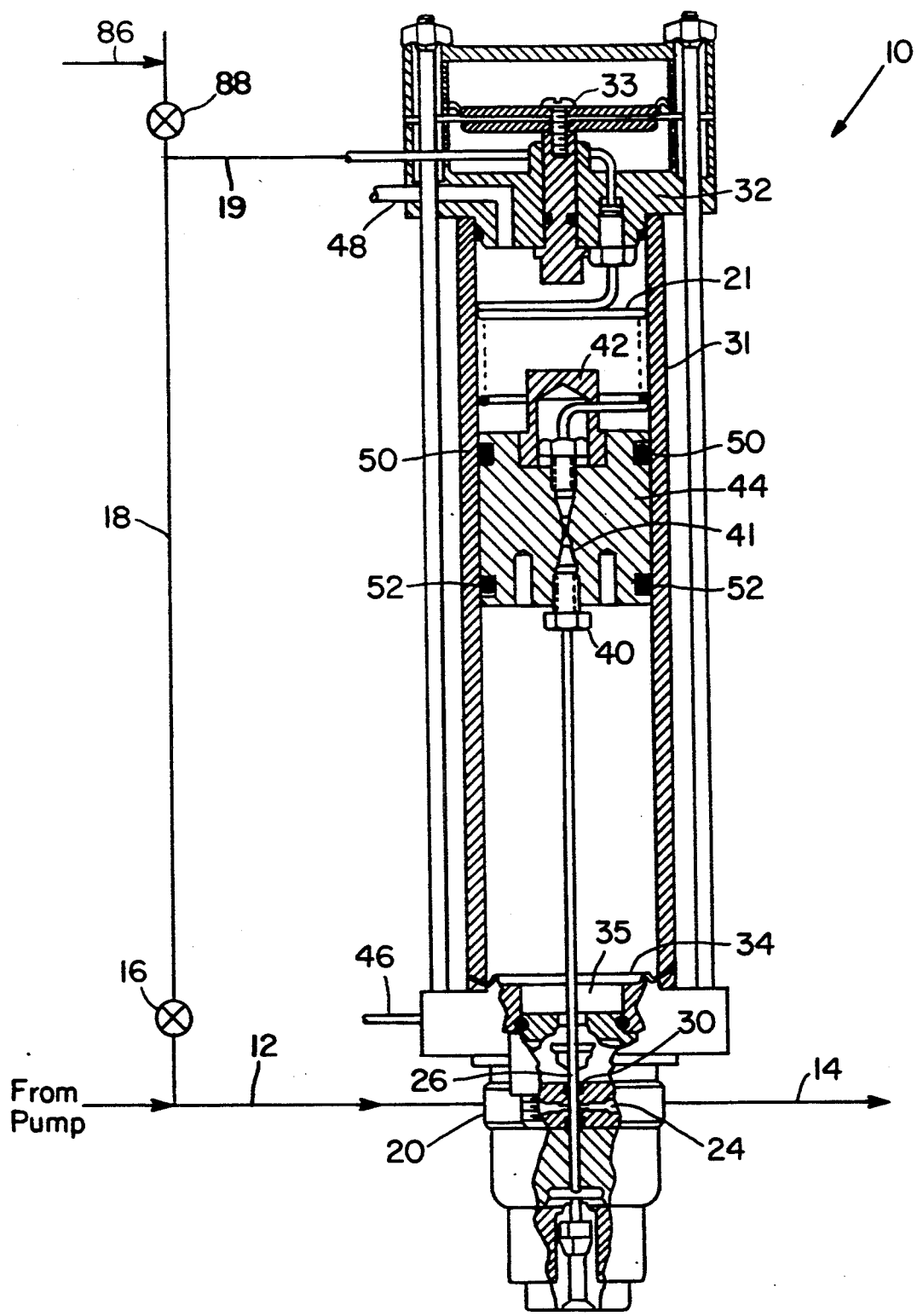
FIG. 1 shows the injection assembly of this invention.
Figure 2:
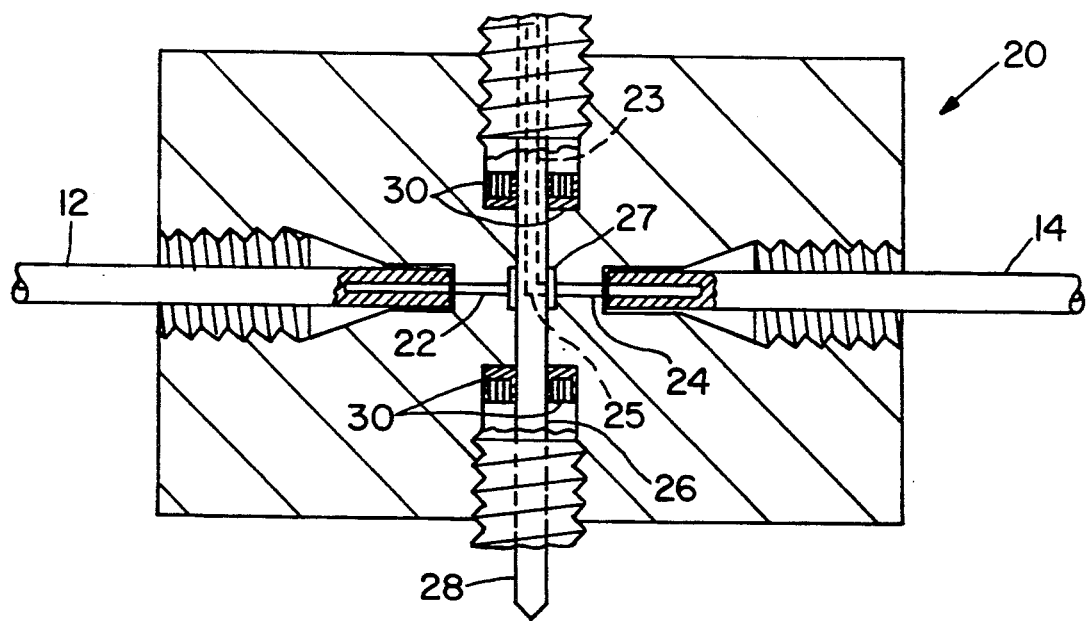
FIG. 2 is a cross-sectional view showing the seal in a liquid chromatography injection apparatus.

Referring to FIG. 1 the injection apparatus of this invention 10 includes a conduit 12 extending from a pump (not shown) which supplies a carrier solvent into the injection apparatus 10 and, communicates with an outlet conduit 14 and thence to a chromatographic column (not shown). As shown in FIG. 2, the liquid proceeds through a needle valving block 20 comprising an inlet port 22 and an outlet port 24 communicating with conduits 12 and 14, respectively. The sampling conduit comprises a modified hypodermic needle 26 which includes an axial passageway 23 and a radial passageway 25 which communicates with outlet Port 24. The hypodermic needle 26 is adapted for reciprocating vertical movement within block 20. When the needle 26 is in its raised position, annular space 27 is Positioned adjacent the radial conduit 25 so that solvent passing through conduit 12 and inlet 22 can pass about the outside surface of the hypodermic needle 26 and entrain sample being injected from conduits 23 and 25 into outlet 24.

Referring again to FIG. 1, in a first mode of operation, a valve 16 in conduit 18 is closed. When valve 16 is open to establish the sample injection mode, liquid from the pump will flow through conduit 12 and also flow through conduit 18 and conduit 19 into extensible tubing 21 and thence through needle 26, to port 24, conduit 14 and to the chromatographic column (not shown). The connection means of needle 26 to piston 44 is formed with nut 40 and ferrule 41. Piston 44 can be pneumatically operated. The piston 44 moves within a cylindrical housing 31 having a top housing plate 32 having a positioning nut 33 and a lower housing plate 34 which has a central channel 35 which continues into block 20 and within which needle 26 reciprocates. Air to raise the piston 44 and the needle 26 enters conduit 46 and air to lower the piston 44 enters conduit 48. These air connections are connected to a pneumatic control system (not shown). The piston 44 is provided with lip seals 50 and 52. Travel of the piston 44 can be adjusted by modifying the vertical position of positioning nut 33.

The cleaning of the interior conduits 23 and 25 (see FIG. 2) of needle 26 is easily accomplished. After a sample has been drawn into needle 26 by means of syringe 86 and the needle 26 has been raised to its proper discharge point where conduit 25 facing conduit 24, the valve 88 is closed, valve 16 is opened and most of the solvent flows through conduits 18, 19 and 21. This solvent flow not only sweeps the sample into the chromatographic column (not shown) but it also continues for a sufficient time thereafter to assure that no substantial sample contamination remains in the needle 26.

Referring to FIGS. 2 through 5, the sealing structure of this invention is shown in detail. At positions just above and below annular space 27, it is necessary to provide an efficacious seal means capable of withstanding pressures of up to about 6,000 psig without binding the movement of needle 26 within bore 66. In this connection, it should be understood that the apparatus of this invention is intended to be utilized in analytical procedures wherein, routinely, samples as small as 5 microliters or smaller are processed. Moreover, the chemical sensitivity of the analytical process being used is such that most organic materials of construction can not be utilized because of chemical contamination which would be leached therefrom.

In the apparatus of this invention, the upper and lower seals 30 comprise a jacket 62 having a U-shaped cross section 64 and a central bore 66 through which the needle 26 passes during use of the apparatus. Within U-shaped cross section slot 64 are positioned two springs comprising a cylindrical band 68 and a cylindrical band 70 each of which contains a slot 72 or 74 which extends through the thickness and along the entire axial length of the cylinder 68 or 70 as specifically shown in FIG. 5. The jacket 62 can be formed of ultrahigh molecular weight polyethylene or reinforced fluorocarbon based materials such as those available under the trade designation RULON J by Dixon Corporation. The material forming the jacket should have a good tensile and compressive strength properties. The inner diameter of the spring 68 should be slightly less than the inner axial surface diameter 78 of the jacket 62. The outer diameter of springs 70 should be slightly larger than the diameter of the outer axial surface 80 of the U-shaped cross section 64.

Figure 3:
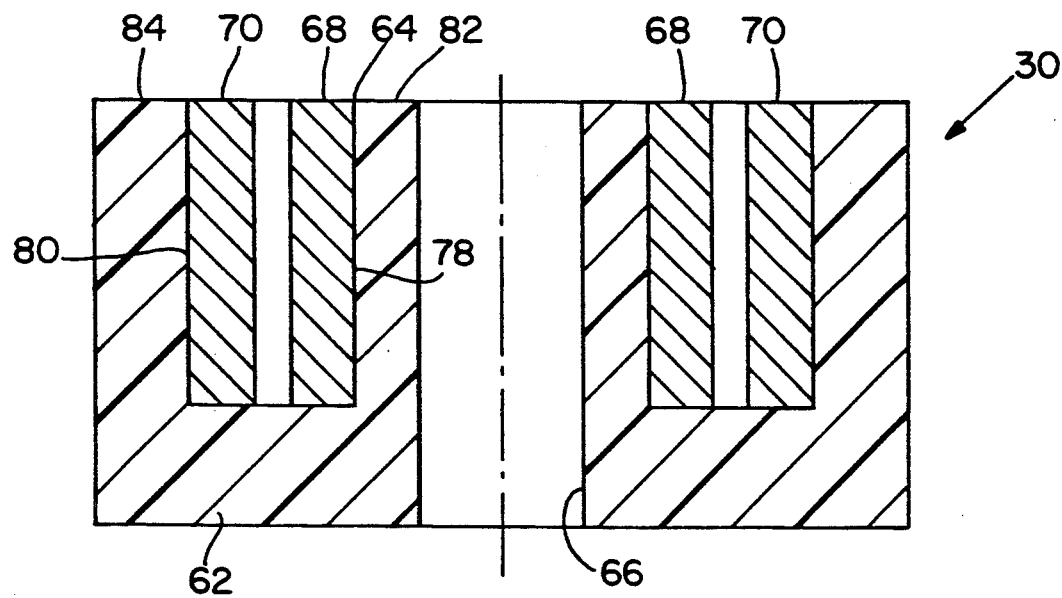
FIG. 3 is a detailed cross-sectional view of the seal of this invention.

As best shown in FIG. 3, the diameter of the inner surface of the U-shaped slot 78 typically is between about 0.087 and 0.001 inches larger than the inner diameter of the spring 68. The diameter of bore 66 typically is between about 0.009 and 0.006 inches less than the outer diameter of the hypodermic needle inserted therein. In use, the pressure exerted by the solvent introduced from conduit 12 into as to compress the spring 68 and expand spring 70 together which in turn exert a pressure on walls 82 and 84 of the jacket such that there is a high elevated pressure exerted at the interface between needle 26 and the wall 82 and at the interface of wall 84 and the housing for the seals shown in FIGS. 3–5. During assembly of seal 30 to needle 26 and housing 20 the needle causes spring 68 to expand and thus increase the pressure of wall 82 on needle 26. Simultaneously the housing 20 causes spring 70 to contract and thus increase the pressure of wall 84 on housing 20.

Figures 4, 5, 6:
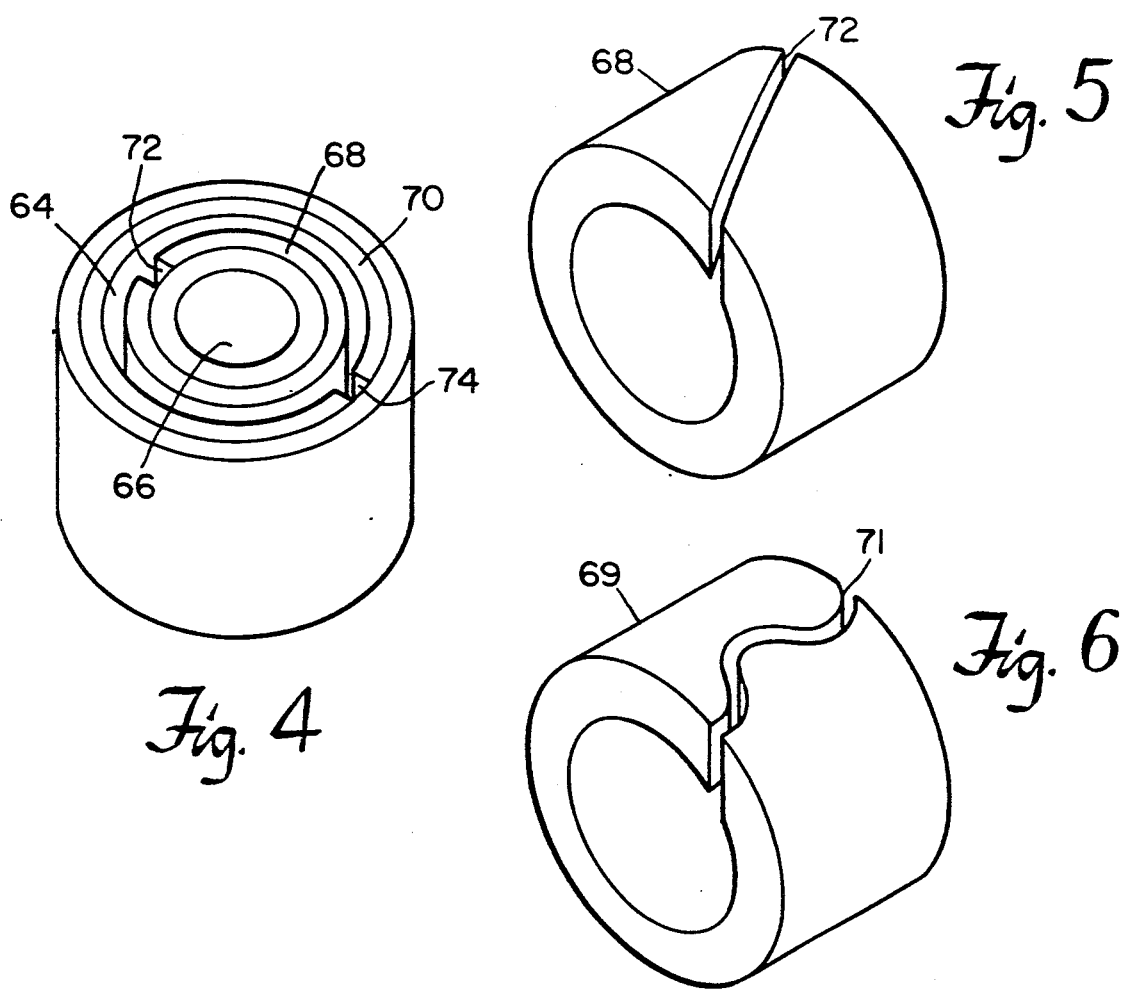
FIG. 4 is an isometric view of the seal assembly of FIG. 3.
FIG. 5 is an isometric view of a cylindrical band spring structure utilized in the present invention
FIG. 6 is an isometric view of an alternative cylindrical band structure utilized in the present invention.

As shown in FIG. 6, the cylindrical band 69 can have a slot 71 which is curved.

Figure 7:
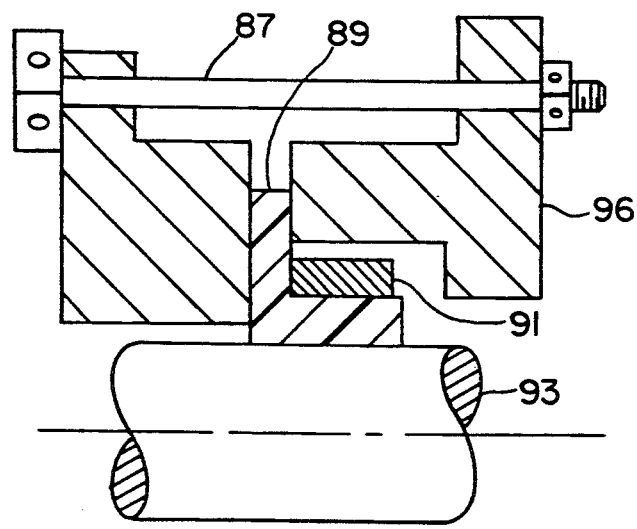
FIG. 7 is a cross-sectional view of an alternative seal structure of this invention.

An alternative seal structure is shown in FIG. 7. which includes only one cylindrical band as a spring. The seal structure includes a clamp 96 which is compressed by means of bolt 87 about a ultrahigh molecular weight polyethylene jacket 89. The cylindrical band 91 of this invention is positioned against jacket 89 to effect a seal about shaft 93 such as a shaft of a pump.

It is to be understood that the seal structure of the present invention is useful in any device wherein there is relative movement, rotational and/or translational, therein an element including the seal structure either moves or remains fixed.

The following example illustrates the present invention and is not intended to limit the same.

EXAMPLE I

This example illustrates that the seals of this invention provide suitable sealing and extend the life of presently available injection apparatus. By utilizing the apparatus in FIGS. 1 through 5, as described herein, no leakage was observed during use with 120,000 injections of sample. In contrast, with the best available apparatus of the prior art utilizing the apparatus shown in FIG 1 with the exception of the seal construction and wherein the seal construction comprises an "O" ring as a spring and a similar elastomeric jacket, only a much value of approximately 12,000 injections were observed without leakage. In addition, with the apparatus of this invention, there was no undue wear on hypodermic needle utilized.

I claim:

1. A fluid seal construction adapted to seal against liquid flow in an axial direction between a cylindrical surface of an outer member and the cylindrical surface of an inner member needle, said construction comprising a jacket having a central bore and a first slot having a U-shaped cross section positioned around said bore, said first slot having an inner axial surface and an outer axial surface, a first spring comprising a hollow first cylinder having a second slot extending through the thickness of said first cylinder and through the entire axial length of said first cylinder, said first spring being positioned within said U-shaped cross section to fit and provide a pressure against said inner axial surface, a second spring spaced apart from said first spring, said second spring comprising a hollow second cylinder having a third slot extending through the thickness of said second cylinder and through the entire axial length of said second cylinder, said second spring being positioned within said U-shaped cross section, coaxial with said first spring to fit and provide a pressure against said outer axial surface.

2. The seal construction of claim 1 wherein said third slot and said second slot extend at an angle to the axis of said first hollow cylinder and said second hollow cylinder respectively.

* * * * *